United States Patent [19]

Klibanov

[11] Patent Number: 4,659,671

[45] Date of Patent: Apr. 21, 1987

[54] ENZYMATIC SEPARATION OF RACEMIC MIXTURES OF HYDROXY COMPOUNDS

[75] Inventor: Alexander M. Klibanov, Boston, Mass.

[73] Assignee: Massachusetts Institute of Technology, Cambridge, Mass.

[21] Appl. No.: 510,335

[22] Filed: Jul. 1, 1983

[51] Int. Cl.$^4$ .................... C12N 9/14; C12N 9/16; C07P 41/00

[52] U.S. Cl. .................... 435/280; 435/195; 435/196

[58] Field of Search .................... 435/D 80, 196, 195

[56] References Cited

U.S. PATENT DOCUMENTS

| | | | |
|---|---|---|---|
| 3,347,752 | 10/1967 | Rauenbusch, Frommer | 435/280 |
| 3,386,888 | 6/1968 | Chibata et al. | 195/2 |
| 3,607,651 | 9/1971 | Moroe et al. | 435/280 |
| 3,635,795 | 1/1972 | Demain et al. | 435/280 |
| 3,666,399 | 5/1972 | Castrantas | 435/196 |
| 3,813,317 | 5/1974 | Benoiton et al. | 435/280 |
| 3,878,043 | 4/1975 | Matta et al. | 435/280 |
| 3,997,543 | 12/1976 | Sokolovsky et al. | |
| 4,022,664 | 5/1977 | Kawamura et al. | 145/2 |
| 4,202,943 | 5/1980 | Suhara et al. | 435/280 |
| 4,226,941 | 10/1980 | Groi et al. | 485/280 |

OTHER PUBLICATIONS

Neuhas et al. *Biochem. Prepr.* vol. 6, p. 75, 1958.

Bamann et al. *Huppe Seyler's 2 Physical Chem. Bd.* 349, pp. 192—196, (1988).

Bamann et al. *Huppe Seyler's 2 Physical Chem. Bl* 349, pp. 671—676, 1968.

*Enzyme Nomenclature* 1978, Academic Press NY 1979.

Mosbach *Methods in Enzymology* 1976, Academic Press NY vol. XIIV.

Scollar et al. *Biotech. Bioeng.* vol. XXVII 1985, pp. 247–252, "Preparative Resolution of D,L—Threonite Catalyzed by Immobilized Phosphatase".

*Primary Examiner*—Thomas G. Wiseman
*Assistant Examiner*—Robin Lyn Teskin
*Attorney, Agent, or Firm*—Hamilton, Brook, Smith and Reynolds

[57] ABSTRACT

The invention constitutes an enzymatic method for resolution of a racemic mixture of hydroxy compounds. A D,L mixture of the hydroxy compound is phosphorylated to form the D,L monoorthophosphate esters of the hydroxy compound. Thereafter, the D,L mixture of phosphorylated compounds is treated with a stereospecific phosphatase, such as wheat germ acid phosphatase, which causes the hydrolysis of substantially only one optical isomer of the monoorthophosphate ester. The resulting hydrolyzed isomer of the hydroxy compound is then separated from the remaining monoorthophosphate ester.

9 Claims, No Drawings

ENZYMATIC SEPARATION OF RACEMIC MIXTURES OF HYDROXY COMPOUNDS

BACKGROUND

Optical isomers are molecules which are made up of the same number and kind of atoms, and which have virtually identical physical properties and structure, except that they have different effects upon polarized light. Each individual isomer of a pair of optical isomers has an equal and opposite effect on polarized light, that is, each isomer causes the plane of polarized light to rotate to the same degree but in the opposite direction. This rotation of the plane of polarized light is known as optical rotation, and a molecule which causes optical rotation is said to have optical activity.

The existence of optical isomers is explained by the three-dimensional spatial configuration of carbon atoms. A carbon atom with four attached substituent groups has a tetrahedral structure. If all of the four substituents are different, the carbon atom is said to be asymmetric or chiral. This indicates that the molecule as a whole is asymmetric.

An asymmetric molecule may have two different geometrical configurations. The two configurations are nonsuperimposable mirror images. Nonsuperimposable mirror image structures of an asymmetric molecule are called enantiomers.

Enantiomers have identical physical properties, except that they rotate a plane of polarized light in opposite directions. An enantiomer which rotates a plane of polarized light in the clockwise direction—as determined by an observer facing the emerging beam of light—is dextrorotatory. The sign of rotation is taken as positive. The letter, d, standing for dextro- , and the notation (+), standing for positive rotation, are used interchangeably to designate a dextrorotatory enantiomer. An enantiomer which rotates the plane of polarized light in a counterclockwise direction is called levorotatory and the letter, l, standing for levo- , or the notation (−), is used to designate the levorotatory enantiomeric form.

Quantitative measurements of the optical activity of asymmetrical compounds are usually reported as specific rotation, denoted by the symbol $[\alpha]$. Specific rotation is defined by the following equation:

$$[\alpha] = \frac{\text{observed rotation in degrees (°)}}{\text{length of sample (dm)} \times \text{conc(g/ml)}}.$$

When specific rotations of pure liquids are reported, the density of the liquid replaces the concentration term in the equation. If the measurement is made with a pure liquid of unknown density, the result is reported as $\alpha$ (no bracket).

If the variables in the denominator of the above equation are kept constant, the observed rotation is characteristic of the optical isomer examined. Generally, the symbols $[\alpha]$ and $\alpha$ are accompanied by a subscript which indicates the wavelength of the light source used in the measurement, most often the D line of sodium (589 nm), and a superscript which indicates the temperature at which the measurement was performed, often 25° C. The rotational value is preceded by a positive or negative sign indicating the direction of the rotation.

The specific rotation of an optical isomer may be measured in a device called a polarimeter. Such a device contains a means for converting ordinary light into plane polarized light, such as a Nicol prism, and a means for assessing the extent of rotation of the plane of polarized light after it has been passed through a sample solution of the optical isomer.

As explained, the d or (+) and the l or (−) notation refers to a physical property of an isomer—the direction in which the isomer causes a plane of polarized light to rotate. The actual geometric configuration of the isomers, however, is signified by a different notation. It is designated by the letters D or L or R and S. Unfortunately, no simple relationship exists between the sign of rotation and the configuration of the isomer. Hereinafter, to distinguish between optical isomers, the form of notation signifying the geometric configuration of the isomer will be used.

A mixture containing equal amounts of two enantiomers is called a racemate or a racemic mixture. Predictably, such mixtures do not rotate polarized light. The clockwise and counterclockwise rotation cancel out.

Ordinarily mixtures of enantiomer usually are perfectly racemic (equimolar amounts of each optical isomer). Under some circumstances, however, one enantiomeric form will be present in excess. The enantiomeric excess (ee) of an isomeric form is designated by a value of from 0 to 100%. Perfectly racemic mixtures have an ee value of 0%; a pure solution of one enantiomeric form has an ee value of 100%.

Racemic mixtures may be formed by converting an enantiomer of either the D or L form into a mixture of enantiomers. This process is called racemization. A common way of inducing racemization is by heating a solution of single enantiomer. Racemization can be monitored by observing the loss of optical activity in the solution over time.

In nearly all chemical procedures for the synthesis of asymmetric compounds, the product is a racemic mixture of the optically active forms, rather than an individual optically active isomer.

It is often important to isolate one optical isomer because in many cases, only one of the optical isomers possesses the biological or other functional activity. In order to obtain the biologically or functionally active isomer in substantially pure form, without the presence of the non-active isomer, the D and L isomers must be separated from each other.

The separation of a racemic mixture into its individual enantiomers is termed resolution. There are several existing methods for resolving racemic mixtures. The simplest, but most tedious and only occasionally applicable, is manual separation. Its application is restricted to the few cases where isomers of like configuration crystallize together to form observably different asymmetric crystals. The D and L forms of sodium ammonium tartrate, for example, may be resolved by this procedure. Another method involves the use of an enzyme which selectively degrades one isomer in the mixture.

Hydroxy compounds have a wide variety of practical uses as pharmaceuticals, flavorings, agricultural chemicals and food additives. Some of the better known examples of such compounds are threonine, malic acid, tartaric acid, menthol, carnitine and the drugs, ephedrine, octopamine, epinephrine and phenylephrine. Many useful hydroxy compounds, including those listed, have at least one chiral carbon atom. These include compounds in which the hydroxy group is attached directly to the chiral carbon atom and those in which it is attached to a carbon atom other than the chiral carbon atom. These hydroxy compounds are assymmetric and may exist in either the D or L isomeric form. In most cases, only one optically active form is biologically active. Standard procedures for the chemical synthesis of such compounds yield racemic mixtures.

The amino acid threonine cannot be synthesized by the human body and is therefore called an "essential" amino acid. It must be acquired preformed in the diet. Consequently this essential amino acid is used widely as a food additive. However, only the L form of threonine is utilized by the human body; its counterpart D-threonine cannot be utilized and therefore lacks nutritive value. For this reason it is highly desirable to obtain L-threonine in pure form. This necessitates separation of the D and L enantiomers which are both formed in the standard chemical syntheses. Unfortunately the conventional techniques for the resolution of racemic mixtures of hydroxy compounds, some of which have been described, are laborious, time-consuming and relatively inefficient.

DISCLOSURE OF THE INVENTION

This invention constitutes an enzymatic method for resolution of racemic mixtures of hydroxy compounds.

The method takes advantage of the fact that certain phosphatases—enzymes which hydrolyze phosphate esters—are stereospecific, that is, they hydrolyze one optical isomer of a phosphate ester much faster than they hydrolyze the other. Specific example of phosphatases which have been found to exhibit this preferential or stereo-selective activity are wheat germ acid phosphatase and potato acid phosphatase.

The method of this invention exploits the preferential activity of certain phosphatase enzymes. According to the method, hydroxy compounds are first chemically converted to their respective phosphate esters and then treated with a stereospecific phosphatase. The sterospecific phosphatase may be an acid or alkaline phosphatase. The phosphatase preferentially hydrolyzes one optical isomer of the phosphate ester. Because of this preferential enzyme action, one optical isomer of the phosphate ester is converted to the corresponding optical isomer of the hydroxy compound while the other optical isomer of the phosphate ester remains substantially unchanged. As a result, the difficult task of separating optical isomers of the hydroxy compound is converted to the relatively simple task of separating the phosphate ester from the hydroxy compound. Because the physical and chemical properties of the phosphate ester and the hydroxy compound differ substantially, they can be easily separated by differential precipitation or by existing chromotagraphic techniques, such as liquid chroma- tography.

BEST MODE FOR CARRYING OUT THE INVENTION

The method of this invention may be used to resolve racemic mixtures of any chiral primary, secondary, or tertiary alcohols. This includes hydroxy compounds in which the hydroxyl group is attached to the chiral carbon atom and those in which the hydroxyl group is attached to a carbon atom other than the chiral carbon atom.

A mixture of isomers of a hydroxy compound is phosphorylated to produce a D,L mixture of the corresponding monoorthophosphate ester of the hydroxy compound. Any conventional method for the synthesis of monoorthophosphates of hydroxy compounds may be employed for this purpose. Threonine, for example, may be phosphorylated using the reagent phosphorus oxychloride according to the method of phosphorylating D,L serine developed by Neuhaus and Korkes, *Biochem. Prepn.* 6:75 (1958).

The racemic mixture of phosphorylated hydroxy compound is then treated with a stereospecific acid or alkaline phosphatase. Ideally, a phosphatase enzyme which virtually exclusively hydrolyzes a single optical isomer should be employed.

Wheat germ acid phosphatase is a preferred enzyme because it exhibits a very high degree of preferential hydrolysis. However, any stereospecific phosphatase may be used, although for those enzymes having less preferential activity, resolution is compromised. For example, potato acid phosphatase is stereospecific (selectively hydrolyses L isomers) and may be used instead of, or in combination with, wheat germ acid phosphatase.

As shown in the table below, wheat germ acid phosphatase is capable of hydrolyzing O-phospho-L-threonine at a 25-fold greater rate than it hydrolyzes the D isomer of O-phosphothreonine, as indicated by a comparison of the maximal velocity of the enzyme for each substrate. Potato acid phosphatase hydrolyzes the L-isomer about 10 times more rapidly. The table also illustrates that stereospecificity is not a property of all phosphatases. Calf intestine alkaline phosphatase and *E. coli* alkaline phosphatase show similar V and $K_m$ values for both isomers of phosphothreonine.

KINETIC PARAMETERS OF THE HYDROLYSIS
OF D- AND L- O—PHOSPHOTHEONINES CATALYZED
BY DIFFERENT PHOSPHATASES

| ENZYME | V, moles/min · mg protein | | $K_M$, mM | |
|---|---|---|---|---|
| | L- | D- | L- | D- |
| Wheat Germ Acid Phosphatase | 0.22 | 0.009 | 1.9 | 11 |
| Potato Acid Phosphatase | 3.6 | 0.38 | 1.4 | 9 |
| Calf Intestine Alkaline Phosphatase | 3.4 | 2.6 | 25 | 22 |
| *E. coli* Alkaline Phosphatase | 28 | 33 | 17 | 25 |

V is the maximal velocity of the enzymatic reaction and $K_m$ is the substrate concentration at half maximal velocity.

Often, it is desirable to immobilize the phosphatase by attaching it to a solid phase such as a gelatinous material before bringing the enzyme into contact with the phosphate esters. Immobilization of the phosphatase facilitates separation of the enzyme from the reaction mixture upon termination of the reaction. Optimal parameters for immobilization of the phosphatase will vary depending upon the particular enzyme chosen, but may be established by routine experimentation.

After treatment of the racemic mixture with the phosphatase, the hydrolyzed isomer and the unhydrolyzed phosphate ester are separated by extraction, crystallization or ion exchange chromatography.

Following separation of the hydrolyzed isomer, the unhydrolyzed, phosphate ester of the counterpart isomer may be hydrolyzed non-enzymatically, for example, by acid or alkaline hydrolysis. In this way, the counterpart isomer of the hydroxy compound may be obtained in substantially pure form.

Alternatively, the remaining phosphate ester may be made to undergo racemization (for example, by heating) and the resulting racemic mixture submitted to the phosphatase treatment. By repeating this cycle, the original racemic mixture of the hydroxy compound may be converted substantially to a single optical isomer of the hydroxy compound.

The procedure for resolution of a racemic mixture according to the invention is illustrated by the following scheme. Hydroxy compounds of the general formula given in the scheme are secondary alcohols wherein the hydroxy group is attached to the chiral carbon atom. However, as mentioned previously, primary and tertiary alcohols as well as hydroxy compounds in which the hydroxyl group is attached to a carbon atom other than the chiral carbon atom may also be resolved by the method as outlined. The phosphatase represented in the scheme is one that preferentially hydrolyzes the L isomer of the phosphate ester. Alternatively, a phosphatase which hydrolyzes the D isomer may be used.

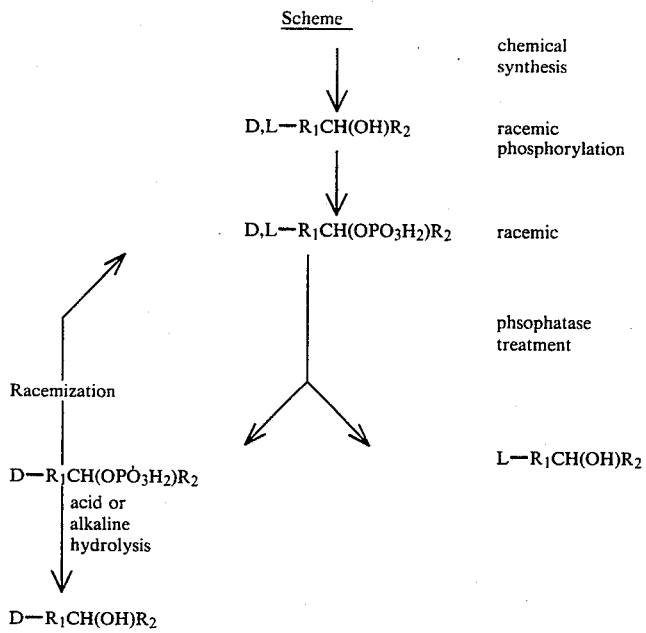

The following examples show the resolution of racemic mixture of threonine and 1-chloro-2 propanol.

EXAMPLE 1

Synthesis of D,L-Phosphothreonine

The synthesis of D,L-phosphothreonine was adapted from the method of Neuhaus and Korkes for synthesis of D,L phosphoserine. The chemical equations are:

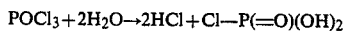

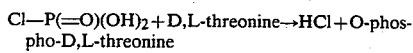

Phosphorus oxychloride (POCl$_3$) (93.6 ml or 1.0 mole) was added to H$_2$O (36 ml or 2.0 moles) drop by drop over 1 hour period with stirring. The solution was left to stir and evolve HCl for an additional hour. Then, 12 grams (0.1 mole) of D,L-threonine was added to the solution over 30 minutes. An additional 30 minutes was needed to dissolve all of the added threonine. After all the threonine was dissolved, the solution was placed in a water bath for 6 hours at 60° C. The ee value of the D,L mixture was 0.

After this time, the solution was extremely foamy and no further evolution of HCl was observed. To quench the reaction, 14.4 ml (0.8 mol) of water was added. The water was added slowly, because considerable heat was generated.

Next, 60 ml 1N HCl was added to hydrolyze polyphosphates, after which the solution was placed in boiling water bath for 20 minutes.

After cooling, 300 ml EtOH and then 60 ml Et$_2$O each added over a ten minute period. The solution was kept in the refrigerator overnight. On the following day, the precipitate formed was filtered out and washed with ethanol and ethyl ether, then dried in a dessicator under reduced pressure. The crude weight of the precipitate was 17.1 g and the crude yield was 85%. A ninhydrin assay gave 84 molar % threonine and phosphothreonine. A phosphothreonine assay (enzyme hydrolysis) gave 85 molar % phosphothreonine. Hence, there was no appreciable threonine impurity. Most of the impurity was attributed to inorganic phosphate. Because there was little if any threonine in the crude precipitate, no further purification was necessary for preparative resolu- tion.

The phosphothreonine was recrystallized by the following procedure. The crude precipitate was dissolved in boiling water, 20 ml H$_2$O per gram of crude precipitate. The solution was cooled and filtered, then 5 ml EtOH per gram of crude precipitate was added. The yield was generally about 60%. The recrystallized phosphothreonine ranged from 97–99% pure with the remainder being inorganic phosphate.

Preparative Resolution

I. Enzyme Immobilization Procedure (Preparation of 2.5 ml, 4% carrageenan gel).

A four per cent carrageenan solution was made by adding 0.04 g of carrageenan to 1 ml water in a test tube. The solution was heated in a boiling water bath, during which the solution was stirred vigorously and the temperature was not allowed to exceed 90° C. After all the carrageenan was dissolved, the test tube was removed from the bath while stirring was continued. When the solution cooled to 39° C., 1.5 ml of wheat germ phosphatase solution (100 mg/ml) was added immediately and the resulting solution was stirred to homogeneity. At 37° C. the gel began to harden. When temperature of the gel reached 25° C., the test tube was placed in an ice bath. After one half-hour, the gel was removed from the tube, cut up into small pieces, and placed in 9 ml 0.5M sodium phosphate solution (pH 7.0) in order to protect active sites of the enzyme. After ½ hour, 1 ml of chilled 25% glutaraldehyde solution was added (giving 2.5% solution) to cross-link the entrapped enzyme. Solution was put in the refrigerator for ½ hour. The gel was filtered out and washed with 500 ml 0.1M citrate (pH 5.6) to remove phosphate. The gel was hardened by adding it to an ice cold 0.3M KCl solution for ½ hour after which it was filtered out and washed with 50 ml 0.1M citrate (pH 5.6).

II. Hydrolysis Procedure

A 0.4M solution of DL-phosphothreonine was prepared by adding 7.96 g crude DL-phosphothreonine to 96 ml $H_2O$ and adjusting the pH to 5.6 with approximately 4ml 10N NaOH. The phosphothreonine dissolved with addition of NaOH.

Ten 2.5 ml volumes of 4% enzyme-containing gels were added to the solution. The resulting suspension was shaken vigorously at 37° C. After 1 day (to allow diffusion of solution into gel) a ninhydrin assay was performed to determine the equilibrium concentration of threonine and phosphothreonine—340 mM.

The solution was filtered by gravity and 97 ml of filtrate was collected. Along with the gel, a white fibrous precipitate was filtered out. The filtrate was yellow indicating impurity in enzyme preparation. The flask was washed with 20 ml $H_2O$. A few gel pieces were washed in 2 L of 0.1M citrate (pH 5.6) and then tested for activity. One quarter the enzymatic activity of freshly prepared gel was measured.

III. Separation Procedure

The 97 ml of filtrate and the 20 ml of washing were combined in a 400 ml beaker. By calculation, the solution contained: 1.96 g of L-Threonine and 3.18 g of D-phosphothreonine. (A calculated 15% loss was due to product diffused into the gel; this loss could be eliminated by washing gel more thoroughly.)

The pH which measured 5.9 was lowered to 1.9 with 6.2 ml 6N HCl. 192 ml ethanol was added over 20 minutes in order to precipitate D-phosphothreonine. Simultaneously 3.35 ml 6N HCl was added to maintain pH at 1.9±0.1. 2 ml $H_2O$ was used to wash precipitate off the electrode. The solution was kept in the refrigerator overnight.

The D-phosphothreonine was filtered out in Buchner funnel and dried in vacuum desiccator. The weight collected was 2.9 g. The yield was 88%. 1.1 g of crude precipitate was recrystallized by dissolving in 15 ml $H_2O$ with heating. The solution was cooled and filtered. 5 ml ethanol was added. After 1 hour solution was put in the refrigerator. Recrystallized D-phosphothreonine filtered out and washed with ethanol; 0.8 g was collected.

The concentration of threonine in solution was calculated to be 54 mM. A ninhydrin assay gave 52 mM which was in good agreement with calculated amount.

500 ml $H_2O$ and 2 drops phenolphthaleine were added. To remove phosphate, $Ca(OH)_2$ was added until the solution turned pink. The precipitate was filtered out and washed with 50 ml $H_2O$. About 200 g dry ice added to remove $Ca^{+2}$. The solution was left overnight then filtered.

After the threonine solution was rotoevaporated a yellow gummy residue remained. An attempt was made to recrystallize the threonine from $H_2O$/EtOH but it was unsuccessful. The threonine came out as an oil. The threonine was evaporated again to a yellow gummy residue, and then redissolved in 7 ml hot $H_2O$. 3 ml hot $H_2O$ was used to wash flask. Upon addition of 40 ml EtOH threonine precipitated as oil which eventually solidified. The solution was left overnight in the refrigerator.

Crude L-threonine filtered out and dried in vacuum desiccator. The amount collected was 1.4 g; the crude yield was 70%. 0.5 g of the L-threonine was dissolved in 1.5 ml of hot $H_2O$. The solution was cooled and filtered. The addition of 3 ml EtOH caused recrystallization. After one hour, solution was put into the refrigerator. 0.2 g of recrystallized L-threonine was collected.

IV. Characterization of Products

Ninhydrin Assays of solutions of the crude and recrystallized products show that the crude and recrystallized D-phosphothreonine samples and the recrystallized L-threonine sample were substantially pure. The crude L-threonine sample was only 75% pure.

To check nature of impurity in crude L-threonine, inorganic phosphate and D-phosphothreonine levels were measured by phosphate assay of a 100 mM solution. The percent phosphate was 0.0668 and the percent phosphothreonine was 0.075. Thus the impurity was not due to either of these. The impurities may have come from the protein or enzyme preparations.

The optical rotation value of the D-phosphothreonine prepared by the resolution procedure was compared to the optical rotation value of D-phosphothreonine prepared from D-threonine. The concentration of each solution was 2.58g/100 ml. The following results were obtained:

$\alpha_{synthesized} = 0.225$; $[\alpha]_D = 8.72$ $\alpha_{resolved} = 0.219$; $[\alpha]_D = 8.48$; ee = 97%

Also, the optical rotation value of the L-threonine prepared by the resolution procedure was compared to that of L-threonine obtained from Sigma Chemical Company. The concentration of each solution was 0.958g/100ml. The results were as follows:

$\alpha_{Sigma} = -0.270$; $[\alpha]_D = -28.2$ $\alpha_{resolved} = -0.266$; $[\alpha]_D = -27.8$; ee = 99%

EXAMPLE 2

Resolution of D,L-1-chloro-2-propanol

Synthesis of 1-Chloro-2-Propanol Phosphate 20 g of 1-chloro-2-propanol (0.211M) was added to 38 g of chilled $POCl_3$ (0.248M) in an ice bath (at 1° C.), and the solution was allowed to sit for 4 hours at that temperature. Then the reaction mixture was heated at 100° for 1 hour and poured into 120 g of ice, whereupon the oil separated from the aqueous phase. Addition of 1 l $H_2O$ and 150 ml KOH (1M) under vigorous stirring resulted in a clear solution. Excess phosphate was removed with $Ba(OH)_2$ which was added until pH 10–12 was reached. Excess $Ba^{2+}$ was removed from the filtrate by addition of dry ice or $CO_2$ gas. The filtrate was concentrated by rotary evaporation of 500 ml $H_2O$. The ester was precipitated by addition of an equal volume of EtOH, the precipitate was dried at 105° C. The yield of 1-chloro-2-propanol phosphate was 50% (36.4 g).

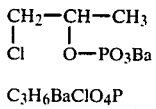

$C_3H_6BaClO_4P$

Enzymatic Resolution Procedure

A 20 mM solution of barium 1-chloro-2-propyl phosphate was mixed with 10 mg/ml acid phosphatase from wheat germ. The reaction mixture is placed in a 37° C. bath until a 50% conversion was reached. The alcohol generated by hydrolysis was extracted with ether and the remaining solution was recycled for further hydrolysis of the remaining enantiomer with the alkaline phosphatase from calf intestine.

Industrial Applicability

The invention constitutes a method for resolution of racemic mixtures of asymmetric hydroxy compounds. Usually, only one isomeric form of an hydroxy compound, either the D or the L form, is biologically active. Typically, procedures for synthesizing hydroxy compounds yield racemic mixtures of the biologically active and inactive forms. Thus, this invention provides a method of preparing the desired biologically active optical isomer of a variety of chemicals, food additives, and drugs in substantially pure form.

I claim:

1. A method for resolution of a racemic threonine, comprising the following steps:
    a. reacting the racemic threonine and phosphorus oxychloride to form a monoorthophosphate ester of threonine;
    b. contacting the monoorthophosphate ester with wheat germ acid phosphatase under conditions whereby said phosphatase preferentially hydrolyzes the L-monoorthophosphate ester of threonine to yield L-threonine; and
    c. separating L-threonine; and the monoorthophosphate ester of D-threonine.

2. A method of resolution of a racemic threonine, comprising the steps of:
    a. phosphorylating the racemic threonine to form a monoorthophosphate ester of threonine;
    b. contacting the monoorthophosphate ester with wheat germ acid phosphatase or potato acid phosphatase under conditions such that the phosphatase preferentially hydrolyzes the L-monoorthophosphate ester of threonine to yield L-threonine; and
    c. separating L-threonine and the monoorthophosphate ester of D-threonine.

3. A method of claim 2, wherein the racemic threonine is phorphorylated by reacting the threonine with phosphorus oxychloride.

4. A method of claim 2, wherein the phosphatase is immobilized in a solid phase.

5. A method of claim 2, further comprising the steps of:
    d. inducing racemization of the monoorthophosphate ester of D-threonine; and
    e. subjecting the resulting mixture to steps b and e until a desired amount of the racemic threonine is converted to L-threonine.

6. A method for resolving a racemic mixture of 1,2-dichloro-3-hydroxy propane, comprising the steps of:
    a. phosphorylating the racemic 1-chloro-2-hydroxypropane to form a phosphate ester of 1-chloro-2-hydroxypropane;
    b. contacting the phosphate ester of 1-chlorohydroxypropane with wheat germ acid phosphatase or potato acid phosphatase under conditions such that the phosphatase preferentially catalyzes the hydrolysis of one optical isomer the phosphate ester; and
    c. separating the hydrolyzed optical isomer of 1-chloro-2-hydroxypropane and the phosphate ester of the other optical isomer.

7. A method of claim 6, wherein the racemic threonine is phorphorylated by reacting the threonine with phosphorus oxychloride.

8. A method of claim 2, wherein the phosphatase is immobilized in a solid phase.

9. A method of claim 2, further comprising the steps of:
    d. inducing racemization of the monoorthophosphate ester of 1-chloro-2-hydroxypropane; and
    e. subjecting the resulting mixture to steps b and e until a desired amount of the racemic 1-chloro-2-hydroxypropane is converted to the optical isomer.

* * * * *